United States Patent [19]

Garnick

[11] Patent Number: 5,340,573
[45] Date of Patent: * Aug. 23, 1994

[54] METHOD FOR REDUCING CHOLESTEROL BY CO-ADMINISTERING M-CSF AND CONVENTIONAL CHOLESTEROL REDUCING AGENTS

[75] Inventor: Marc Garnick, Brookline, Mass.

[73] Assignee: Genetics Institute, Inc., Cambridge, Mass.

[*] Notice: The portion of the term of this patent subsequent to Mar. 1, 2011 has been disclaimed.

[21] Appl. No.: 27,918

[22] Filed: Mar. 8, 1993

Related U.S. Application Data

[63] Continuation of Ser. No. 709,451, Jun. 3, 1991, abandoned, which is a continuation of Ser. No. 281,432, Dec. 8, 1988, Pat. No. 5,021,239, which is a continuation-in-part of Ser. No. 170,478, Mar. 21, 1988, Pat. No. 5,019,381.

[51] Int. Cl.$^5$ .............................. A61K 37/02
[52] U.S. Cl. ........................ 424/85.1; 514/2; 514/8; 514/12; 514/21
[58] Field of Search ............... 424/85.1; 514/2, 8, 514/12, 21

[56] References Cited

PUBLICATIONS

Brown, et al., *Ann Review Biochem.* 52:223 (1983).
Brown, et al., *Science* 232: 34–47 (1986).
Clark, et al., *Science* 236:1229–1237 (1987).
Dixon, et al., *Metabolism* 33 (5):400–404 (1984).
Dixon, et al., *Clin. Res. U.S.A.* 30(4):707a.
Dodge, et al., *Ex. Mol. Path.* 36:44–56 (1982).
Fogelman, et al., *J. Immunol.* 131:2368–2373 (1983).
Garnick, et al., *Natl. Amer. Fed. Clin. Res.* 37:260A (1989).
Gould, et al., *Medical Letter:* 87–90 (1987).
Havel, et al., *J. Clin. Invest.* 81: 1653–1660 (1988).
Kokkonen, et al., *PNAS USA* 84:2287–2291 (1987).
Leslie, et al., *Biochem. Biophys. Acta* 711(2):290–303 (1982).
Marx, Jean L., *Science* 239:258–267 (1988).
Motoyoshi, et al., *Lancet:* 326 (1989).
Nimer, et al., *JAMA* 260(22):3297–3300 (1988).
Pfeffer, et al., *PNAS USA* 82(8):2417–2421 (1985).
Rifkin, et al., *Behring Inst. Mitt.* 83:125–133 (1988).
Shimano, et al., *Circulation* 80:0321 (1989).
Wilson, et al., *Fed. Proc. USA* 43(4):3267 (1984).
Wilson, et al., *J. Clin. Oncol.* 7(10):1573–1577 (1989).

*Primary Examiner*—Garnette D. Draper
*Attorney, Agent, or Firm*—Thomas J. DesRosier; Steven R. Lazar; Luann Cserr

[57] ABSTRACT

Methods are presented for improving the lipoprotein cholesterol profile of a mammal. Methods are also presented for removing atherosclerotic lesions from a mammal that has such lesions. The methods comprise administering to the mammal a therapeutic amount of an M-CSF protein in combination with a pharmaceutically acceptable excipient.

4 Claims, No Drawings

METHOD FOR REDUCING CHOLESTEROL BY CO-ADMINISTERING M-CSF AND CONVENTIONAL CHOLESTEROL REDUCING AGENTS

This is a continuation of application Ser. No. 07/709,451, filed Jun. 3, 1991 now abandoned, which is a continuation of 07/281,432, filed Dec. 8, 1988, now U.S. Pat. No. 5,021,239; which is a CIP of 7/170,478 filed Mar. 21, 1988, now U.S. Pat. No. 5,019,381.

INTRODUCTION

Abnormal blood cholesterol levels increase an individual's risk of coronary heart disease. Cholesterol is transported in the body largely through the interaction of the lipoproteins. A great deal of attention has focused on the search for agents that safely and effectively reduce levels of lipoprotein and thus cholesterol in the blood. While blood cholesterol levels can be somewhat reduced through diet modifications, recourse to drug therapy is often required.

Coronary heart disease (CHD) is caused by atherosclerosis which results from the formation of atherosclerotic plaques or lesions. These plaques are build-ups of cholesterol deposited in the arterial wall. The build-up occurs because cholesterol is insoluble in water and thus is not readily removed by the blood. "If cholesterol is to be transported safely in blood, its concentration must be kept low and its tendency to escape from the bloodstream must be controlled." M. S. Brown and J. L. Goldstein, *Science*, 232:34–47 (1986).

Initially, free cholesterol is bound to the surface of high-density lipoproteins (HDL) and coupled to a fatty acid in an esterification reaction. The cholesteryl esters which are formed on the surface of HDL are subsequently encapsulated within low-density lipoproteins (LDL). The cholesteryl ester-containing LDL then enters certain cells through a lipoprotein-specific receptor-mediated-endocytosis. Once inside the cell, the esters are hydrolyzed back to cholesterol and put to constructive use in the formation of steroids and membranes, or it is biochemically modified for safe and efficient removal from the body.

Significantly above average levels of HDL have been associated with reduced risk of CHD, while significantly above average levels of LDL have been associated with increased risk of CHD.

The LDL is the most abundant cholesterol-carrying lipoprotein in the human body and carries about three-fourths of the total cholesterol of normal human plasma. Lowering plasma LDL levels will effect a reduction of serum cholesterol and so decrease the progression of atherosclerosis. Furthermore, because the HDL remove free cholesterol from the plasma and prepare it for encapsulation within the LDL an increased HDL/LDL ratio is generally accepted as representing an improved lipoprotein cholesterol profile.

The importance of maintaining a healthy overall lipoprotein cholesterol profile has recently been made evident. Recent studies suggest that heart disease can strike even individuals having safe levels of total cholesterol if their levels of HDL are low. Thus, not only high levels of LDL, but also low levels of HDL can be very dangerous.

THE INVENTION

My invention provides a method for improving the lipoprotein-cholesterol profile of a patient. As used herein the term "improved lipoprotein cholesterol profile" is one in which the HDL cholesterol/LDL cholesterol ratio is increased. Optimally, the HDL cholesterol level is raised and the LDL cholesterol level is lowered.

More specifically, my invention provides a method whereby HDL levels may be raised and LDL levels may be lowered comprising administering to a mammal an amount of an M-CSF (macrophage colony stimulating factor) protein sufficient to increase the HDL cholesterol/LDL cholesterol ratio.

Because HDLs scavenge serum cholesterol and provide the vehicle by which serum cholesterol is either put to constructive use or modified for safe and efficient removal, then an increased level of HDLC in the patient indicates improved removal of total cholesterol. Improving removal of cholesterol from the bloodstream of the patient reduces the build-up of atherosclerotic plaques and so reduces the patient's risk of coronary heart disease. Additionally, the method of the present invention reduces the LDLC levels, as well as the levels of other lipoproteins and lipids in mammals. Thus, the method of this invention may lower levels of total cholesterol and other lipids in mammals.

The invention further provides a method for removing atherosclerotic lesions even after they have formed. By effecting the regression of atherosclerotic lesions the patient's risk of coronary heart disease is further reduced. Thus, my invention provides methods for both the improvement of a mammal's lipoprotein profile, as well as effecting the regression of atherosclerotic lesions.

Furthermore, I contemplate that other cholesterol reducing agents, e.g. lovastatin, cholestipol, lopid, cholestyramine, probucol, may be administered conjointly with M-CSF to both improve the lipoprotein profile and cause a regression of atherosclerotic lesions in mammals.

The pharmaceutical compositions of the present invention comprise M-CSF (also referred to as CSF-1) and/or granulocytemacrophage colony stimulating factor (GM-CSF) in combination with a pharmaceutically acceptable excipient.

The preferred pharmaceutical composition comprises M-CSF. M-CSF produces colonies that contain primarily macrophages. Long form M-CSF (LCSF-1) has been specifically described by Wong et al., *Science*, 235: 1504–1508 (1987). Its production by recombinant DNA techniques is described in WO87/06954. See also EP 0,261,592; WO88/03173; and EP 0,276,551.

A truncated version of CSF-1 is described in WO86/04607. Kawasaki et al., *Science*, 230:291–296 (1985) describe the cDNA sequence encoding that truncated protein. Variations on that truncated version having deletions or substitutions of hydrophobic amino acids characteristic of a transmembrane region are described in EP 0,249,477. Methods for purifying CSF-1 proteins from natural sources are described in GB 2,016,477; and WO86/04587. See also, S. K. Das et al., *Blood*, 58:630 (1981); publications by E. R. Stanley; and references cited in WO86/04587.

An M-CSF protein, for purposes of this invention, includes the natural proteins, recombinant versions thereof, and derivatives and analogues thereof, which may contain amino acid deletions, substitutions and/or insertions, but retain the characteristic biological activity of M-CSF; which is the ability to proliferate the growth of cells predominantly of the monocyte/macrophage lineage in the standard bone marrow assay of Wong et al., Science, 235: 1504-1508 (1987), and are encoded by DNAs capable of hybridizing to the DNA of the naturally occurring version, which is shown in FIG. 2 of Wong et al. Also included, of course, are naturally-occurring isotypes or allelic variations in the protein or its coding sequence resulting from expression of the protein in different members of a species.

The components of this method should be administered systemically, e.g. intravenously. When parenterally administered, the therapeutic preparations for use in this invention should be in the form of non-pyrogenic, sterile, parenterally acceptable aqueous solutions.

A therapeutically effective dose of M-CSF, i.e. an amount sufficient to increase the HDL cholesterol/LDL cholesterol ratio, is in the range of 1-200 micrograms ($\mu$g)/kg/day. The presently preferred dose is in the range of about 5-150 $\mu$g/kg/day. The methods of the present invention may involve a series of administrations of the pharmaceutical compositions. Such a series may take place over a period of about 7-14 days. One or more series may be administered. Additionally, it is contemplated that the methods of the present invention may be used in chronic treatment for maintaining an acceptable lipoprotein cholesterol profile in a mammal.

The actual dosing regimen utilized in the methods of the present invention will be determined by the attending physician considering various factors which modify the action of drugs, e.g., the condition, body weight, sex, and diet of the patient, the severity of the condition, time and method of administration and other clinical factors.

The following Examples are illustrative of the improvements that may be observed in the lipoprotein profiles of mammals in response to M-CSF administration.

EXAMPLE 1

The patient was a normal cynomologous macaque monkey, weighing approximately 5 kg, and having a cholesterol level as indicated in Table I below. M-CSF was administered by intravenous bolus injection at a dose of 100 $\mu$g/kg/day on days 1-15, 45-59, and 73-87.

This animal demonstrated a persistent reduction in serum cholesterol and LDL cholesterol, and an actual rise in HDL cholesterol.

TABLE I

| Day | Cholesterol | HDL Cholesterol | LDL Cholesterol |
|---|---|---|---|
| 1 | 145 | 66 | 70 |
| 27 | 129 | 68 | 54 |
| 28 | 127 | 79 | 41 |
| 73 | 131 | 71 | 54 |

EXAMPLE 2

The patient was a normal cynomologous macaque monkey weighing approximately 5 kg, and having a cholesterol level as indicated in Table II below. M-CSF was administered by ntravenous bolus injection at a dose of 50 $\mu$g/kg/day on days 1-15, 29-34, and 59-73.

This animal also demonstrated a reduction in serum cholesterol and LDLC and a rise in HDLC.

TABLE II

| Day | Cholesterol | HDL Cholesterol | LDL Cholesterol |
|---|---|---|---|
| 1 | 142 | 79 | 56 |
| 23 | 142 | 80 | 56 |
| 27 | 140 | 85 | 50 |
| 29 |  | 87 |  |
| 85 | 123 | 80 | 36 |

EXAMPLE 3

A female New Zealand white rabbit was cannulated with an INFUSAID$^R$ silicon rubber catheter on one facial vein and a MICRORENETHANE$^R$ catheter on the opposite jugular vein. The catheters were subcutaneously routed and exited between the scapula. A jacket that held an ABBOTT PARKER$^R$ pump was placed on the rabbits and the INFUSAID$^R$ catheter was connected to the pump. The other catheter was heparin-locked for blood sampling.

After a one week recovery period, the rabbit was started on a constant infusion of M-CSF at 100 mg/Kg/day. Blood samples for cholesterol analysis were drawn on days 0, 8 and 15.

This animal demonstrated a consistent reduction in total cholesterol levels, LDL cholesterol levels, and a rise in HDL cholesterol levels.

TABLE III

| Day | Cholesterol | HDL Cholesterol | LDL Cholesterol |
|---|---|---|---|
| 0 | 134 | 21 | 76 |
| 8 | 108 | 26 | 71 |
| 15 | 92 | 27 | 50 |

What is claimed is:

1. In the method for reducing cholesterol levels in a mammal by administering a cholesterol-reducing agent selected from the group consisting of lovastatin, cholestipol, lopid, cholestyramine and probucol, the improvement comprising conjointly administering to said mammal M-CSF; whereby the lipoprotein cholesterol profile is thereby improved.

2. The method of claim 1, wherein the mammal is a primate.

3. In the method for reducing cholesterol levels in a mammal by administering cholestyramine, the improvement comprising conjointly administering M-CSF to said mammal.

4. The method of claim 1, wherein the mammal is a primate.

* * * * *